United States Patent [19]

Bolton et al.

[11] Patent Number: 4,579,826
[45] Date of Patent: Apr. 1, 1986

[54] METHOD AND DEVICE FOR ANALYZING HUMAN BREATH

[76] Inventors: Craig E. Bolton, 20400 Frederick Rd., Germantown, Md. 20874; Stephen M. Roylance, 12210 Glen Mill Rd., Potomac, Md. 20854

[21] Appl. No.: 537,526

[22] Filed: Sep. 30, 1983

[51] Int. Cl.$^4$ .................. G01N 1/22; G01N 21/78
[52] U.S. Cl. .................. 436/132; 128/719; 128/730; 446/202; 422/85; 436/900
[58] Field of Search .............. 422/84, 100, 85; 436/132, 900; 73/864.51, 864.62; 128/730, 716, 719; 446/202, 207, 180, 186, 200, 220, 226; 137/843, 846

[56] References Cited

U.S. PATENT DOCUMENTS

| Re. 27,008 | 12/1970 | Luckey . | |
|---|---|---|---|
| Re. 31,246 | 5/1983 | Adrian et al. . | |
| 392,711 | 11/1888 | Barton . | |
| 743,570 | 11/1903 | Savage | 446/186 |
| 2,041,737 | 5/1936 | Beal | 446/220 |
| 2,062,785 | 12/1936 | Harger . | |
| 2,141,646 | 12/1938 | Ferguson . | |
| 2,591,691 | 4/1952 | Forrester . | |
| 2,867,511 | 1/1959 | Harger . | |
| 3,009,786 | 11/1961 | Luckey . | |
| 3,196,689 | 7/1965 | Forrester et al. . | |
| 3,223,488 | 12/1965 | Luckey . | |
| 3,303,840 | 2/1967 | Etzlinger | 128/730 |
| 3,321,976 | 5/1967 | Jones . | |
| 3,347,636 | 10/1967 | Luckey . | |
| 3,420,224 | 1/1969 | Farr . | |
| 3,426,745 | 2/1969 | Fair . | |
| 3,437,449 | 4/1969 | Luckey . | |
| 3,505,022 | 4/1970 | Luckey . | |
| 3,509,771 | 5/1970 | Moberg et al. . | |
| 3,522,009 | 7/1970 | Borkenstein . | |
| 3,582,274 | 6/1971 | Keyes . | |
| 3,613,665 | 10/1971 | Gorsuch . | |
| 3,622,278 | 11/1971 | Elzinger et al. . | |
| 3,676,073 | 7/1972 | Luckey | 436/181 |
| 3,734,692 | 5/1973 | Lucker et al. | 128/730 |
| 3,821,950 | 7/1974 | Boehringer . | |
| 3,910,261 | 10/1975 | Ragsdale et al. . | |
| 4,277,251 | 7/1981 | Leichnitz . | |
| 4,291,704 | 9/1981 | Petty et al. | 446/202 |
| 4,294,583 | 10/1981 | Leichnitz . | |
| 4,298,010 | 11/1981 | Eckstein et al. . | |
| 4,317,453 | 3/1982 | Heim et al. . | |
| 4,332,771 | 7/1982 | Leichnitz . | |

OTHER PUBLICATIONS

*Shure Winner Catalogue*, No. 130 (1938), p. 1122.

Primary Examiner—Barry S. Richman
Assistant Examiner—Michael S. Gzybowski

[57] ABSTRACT

A device, useful for breath analysis and as an amusement device, comprising a flexible tube which can be extended from a shortened condition to an extended condition, one end of the tube being secured to a mouthpiece unit including both an input opening, through which breath can be exhaled into the tube, and an exhaust opening; spring means for urging the tube to its shortened condition; an escape opening at the end of the tube opposite the mouthpiece unit; and pressure regulating means for opening the escape opening when the tube has been inflated by breath exhaled through the input opening. Advantageously, the tube is a collapsible, non-self-supporting polymeric tube and the spring means is effective to roll the tube upon itself in spiral fashion toward the mouthpiece unit.

24 Claims, 8 Drawing Figures

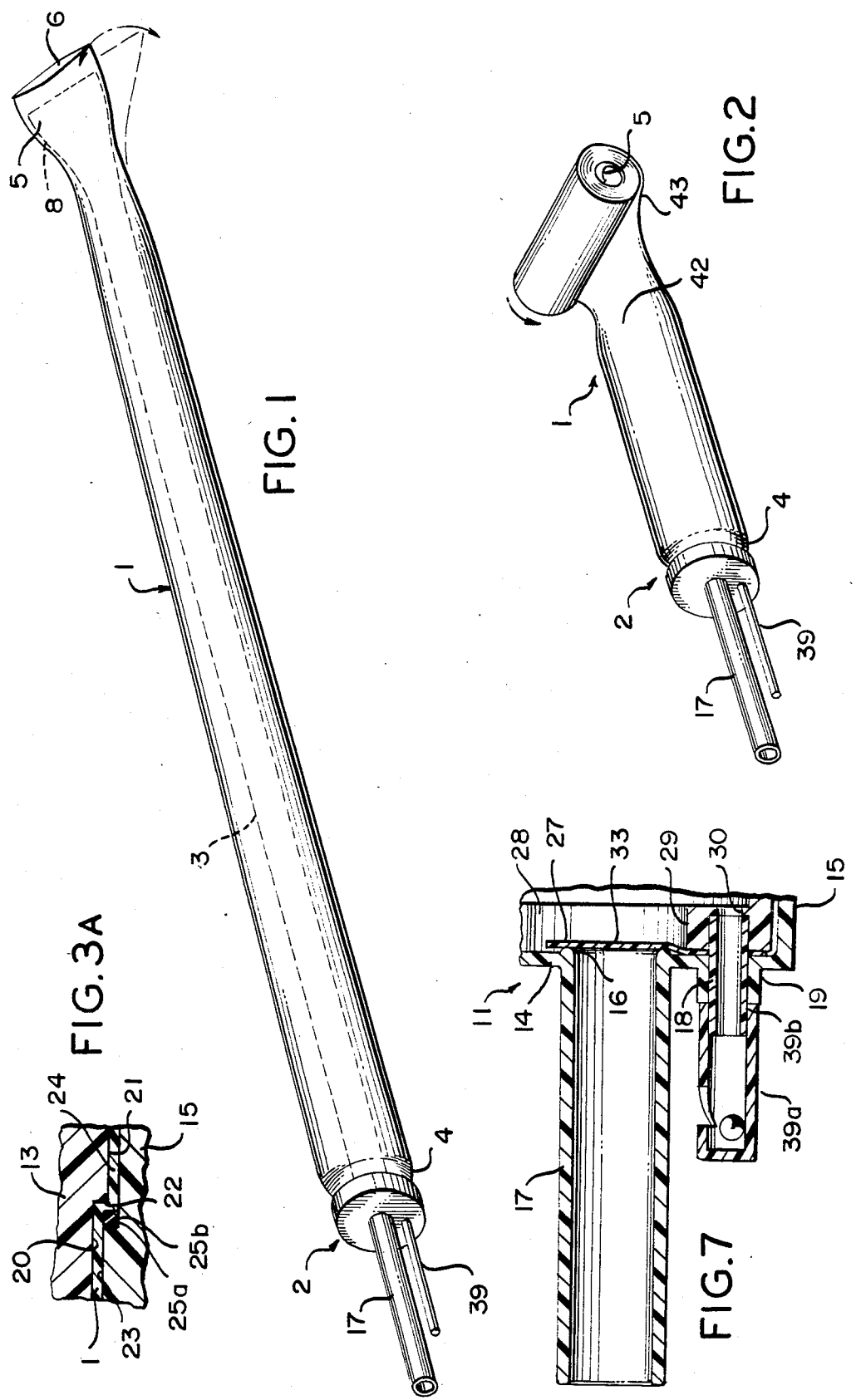

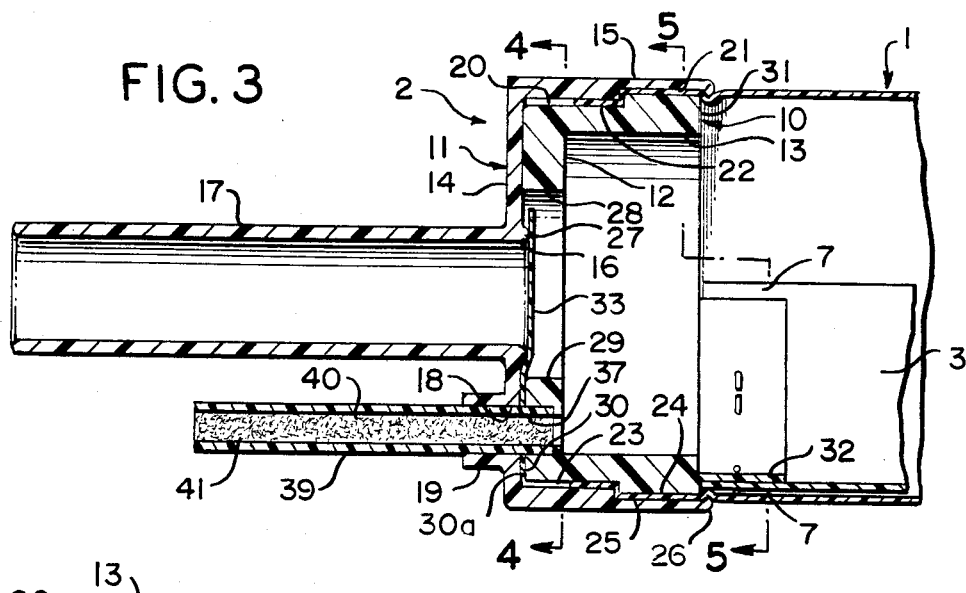
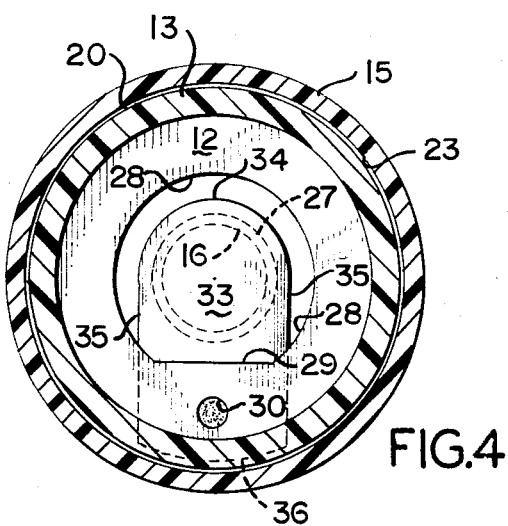
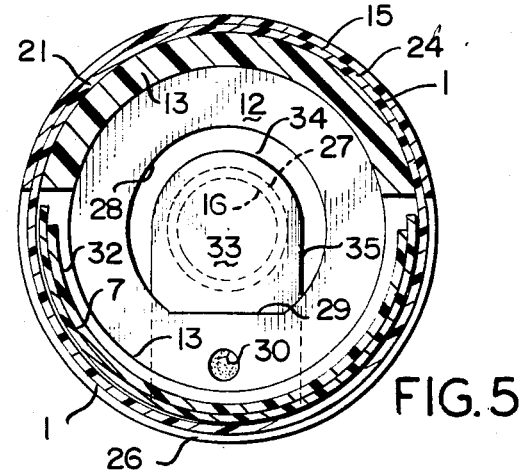
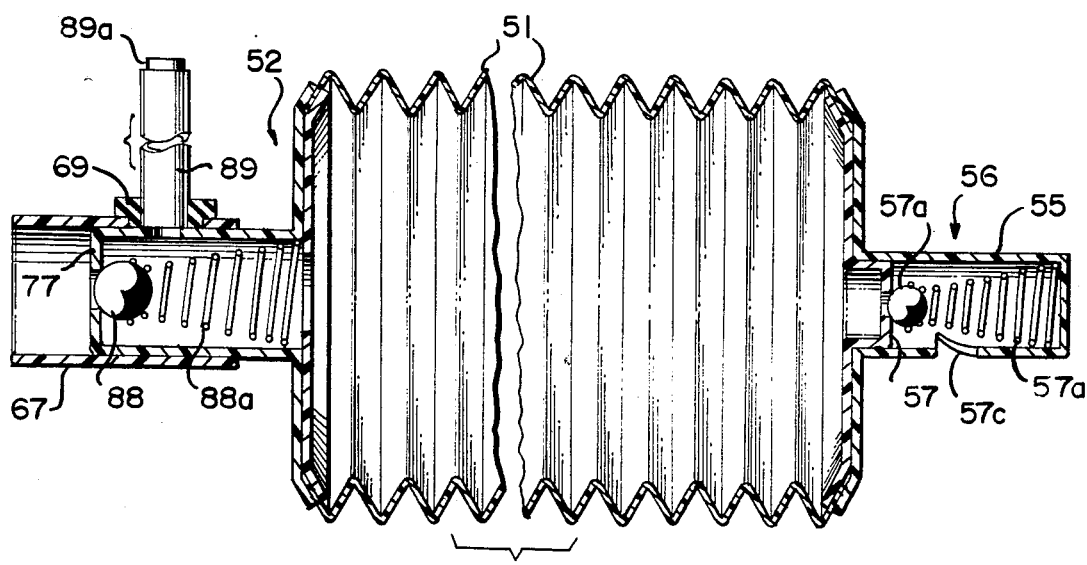

METHOD AND DEVICE FOR ANALYZING HUMAN BREATH

This invention relates to testing or analyzing human breath and particularly to methods and devices for obtaining and presenting for testing or analyses a sample of breath which is of substantially predetermined molar volume and at least primarily alveolar gas.

BACKGROUND OF THE INVENTION

It is frequently desirable to analyze the breath of a human individual to determine whether the breath contains a particular chemical compound, such as ethyl alcohol or carbon dioxide, or a non chemical, such as a particular microorganism. Prior-art workers have provided numerous methods and devices for obtaining samples of breath for such analysis. It was recognized early in this art that obtaining samples of breath to be analyzed presents three main problems. One of the more important and difficult of these problems is to ensure that the sample of breath obtained is at least primarily alveolar gas, i.e., gas contained in the alveoli rather than from the mouth, throat and bronchials. In exhalation, as the lungs contract, breath contained in the mouth, throat and bronchials is necessarily exhaled first, followed by the breath contained in the alveoli of the lungs. Since it is at the alveoli where the exchange of substances between breath and blood ultimately occurs, the concentration of gaseous or vaporous constituents in the alveoli corresponds more closely to the concentration of substances dissolved in the blood. Thus, if a sample of breath is to be analyzed for the presence of constituents which may be present in the blood, the sample of breath analyzed must be at least primarily alveolar gas. Similarly, an alveolar sample is required for best detection of, e.g., microorganisms in the lungs. A usual approach to this problem has been to direct the early portion of exhalation into a first chamber, then to direct the last portion of exhaled gas into a second chamber, the gas collected in the second chamber being the sample for testing or analysis. Methods and devices typical of this approach are disclosed in U.S. Pat. Nos. 2,795,223, Stampe; 3,544,273, McConnaughey; 3,676,073, Luckey; and 3,734,692, Lucker et al. Other prior art workers have adopted the approach of employing only a single chamber, into which all of the breath is exhaled, and providing flow means such that at least some of the breath escapes from the chamber, only the later portion of the exhaled breath being intended to remain in the chamber for testing. Typical methods and devices of this type are disclosed in U.S. Pat. Nos. 1,685,557, Legelsberger, 3,303,840, Etslinger and 3,858,573, Ryan et al. Another problem encountered is that of obtaining a sample of substantially predetermined volume and then presenting the collected sample for testing or analysis. In efforts to solve this problem, it is frequently proposed to employ an elastically expansible container, typically a balloon, to collect the sample, with the elasticity of the balloon acting to expel the collected sample for testing or analysis as the balloon deflates. In other efforts to solve this problem, it has been proposed to employ an inelastic container of such nature that the container can be collapsed by hand pressure to expel the collected sample for testing or analysis, as in the Etslinger and Lucker et al patents, or of such nature that the sample is pumped from the container, as in the Ryan et al patent. In addition to these problems, the trade has imposed the requirement that the device employd to collect and present the breath sample must be simple, inexpensive and difficult for the user to defeat. Though some prior-art devices and methods have achieved commercial acceptance, all suffer from failure to satisfactorily solve at least one of the problems just mentioned and there has been a continuing need for improvement.

OBJECTS OF THE INVENTION

A general object of the invention is to provide an improved method and device for obtaining from a human subject a breath sample which is of substantially predetermined volume and which is at least mainly alveolar gas.

Another object is to provide a device for taking breath samples which is less under control of the individual giving the sample than has been the case with devices heretofor employed.

A further object is to provide such a device which, once the sample has been taken, will automatically deliver the sample at a predetermined relatively constant flow rate for analysis of the sample.

Yet another object is to provide such a device which collects more accurately the required predetermined molar volume of sample gas, and which requires neither manual collapsing of the container nor use of an external device to force the sample from the container.

A still further object is to provide such a device which, though offering improved accuracy and dependability, is not only simple and inexpensive, but also will be viewed by most persons as entertaining, educational and enjoyable to use.

SUMMARY OF THE INVENTION

In general, devices according to this invention comprise an elongated inflatable tube formed of flexible substantially gas impermeable material and adapted for inflation to a regulated pressure by exhaled human breath and defining when inflated a chamber having a predetermined volume substantially smaller than that of the average capacity of human lungs. A mouthpiece is provided which is sealed in gas-tight relationship to a first end of the tube and has a passage therethrough communicating with the interior of the tube. The mouthpiece can be formed integrally with or otherwise affixed to the tube. Valve means is provided to permit a stream of exhaled breath to be blown through the passage in the mouthpiece to inflate the tube and to prevent gas in the inflated tube from escaping back through the passage. Pressure regulator means (located advantageously at the other or second end of the tube) permits gas to exhaust from that end of the tube only when gas pressure in the inflated tube exceeds a predetermined value. Resilient means urges the tube from an inflated state back to a fully deflated state, and can be integral with the tube. An exhaust port is provided adjacent the mouthpiece to deliver the gas contained by the inflated tube to, e.g., an analyzing device carried by the device. In particularly advantageous embodiments, the tube comprises a spiral spring arranged to roll the tube upon itself progressively (from the second end toward the mouthpiece) and, in such embodiments, the end of the tube opposite the mouthpiece is open, save when the spring is allowed to roll that end of the tube upon itself, the open end portion of the tube then coacting with the spring means to constitute a pressure regulator means. Typically, the exhaust port is constructed and arranged to receive in fluid-tight fashion one end of a tube packed with a reagent system for colorimetric analysis of the sample.

According to method embodiments of the invention, the person giving the sample is required to exhale continuously through the mouthpiece until the air in the lungs is essentially exhausted. The exhaled breath pressure inflates the tube and then, overcoming the pressure regulator means, and exhausts through the second end of the tube. When, having continued to exhale at a rate adequate to keep the tube inflated, the person giving the sample can no longer exhale, cessation of exhalation allows the pressure regulator means to effectively close the second end of the tube so that the desired predetermined volume of breath is trapped. Though escape of gas via the input opening can be prevented by simply placing a thumb over that opening, the input opening is advantageously closed by a check valve. With the input opening closed, and the second end of tube now closed by action of the pressure regulating means, the collected sample can now escape only via the exhaust port. The spiral spring rolls up the tube, driving the collected sample out through the exhaust port at a substantially constant flow rate dependent upon, among other factors, the strength of the spring means, the flexibility of the tube and the size of the exhaust port.

In other particularly advantageous embodiments, the tube is of thin polymeric material and is of the type referred to in the plastics trade as a lay-flat tube, one end of the tube is secured to fluid-tight fashion about the mouthpiece and the spring is an initially flat strip of resilient polymeric material which has been deformed into a spiral under the influence of heat, then cooled to return the polymeric material to its original resilient condition.

IDENTIFICATION OF THE DRAWINGS

FIG. 1 is a perspective view of a breath alcohol analyzing device according to one embodiment of the invention, with the tube being fully inflated under the influence of exhalation and maintained inflated while excess breath escapes freely from the open end;

FIG. 2 is a view similar to FIG. 1 but showing the device with the tube rolled spirally upon itself after exhalation has ceased;

FIG. 3 is a longitudinal cross-sectional view, enlarged relative to FIG. 1, of the mouthpiece unit of the device of FIG. 1;

FIG. 3A is a fragmentary cross-sectional view of a modified combination for assuring a fluid-tight seal between the tube and the mouthpiece unit of the device of FIG. 1;

FIGS. 4 and 5 are transverse cross-sectional views taken generally on lines 4—4 and 5—5, respectively, FIG. 1;

FIG. 6 is a longitudinal cross-sectional view of a device according to another embodiment of the invention; and FIG. 7 is a fragmentary longitudinal cross-sectional view illustrating one manner in which devices according to the invention can be equipped with a sounding device.

DETAILED DESCRIPTION OF THE INVENTION

Device Embodiment of FIGS. 1-5

FIGS. 1-5 illustrate one embodiment of a device for carrying out the method, the device comprising a breath-collecting tube, indicated generally at 1, and a mouthpiece unit, indicated generally at 2. Tube 1 is formed of thin polymeric material, such as polyethylene film, and is advantageously of the type referred to in the plastics trade as a lay-flat tube. Fully inflated, the tube assumes a generally circular transverse cross section, but when fully deflated assumes a flat form. Within tube 1 is a spiral spring 3, FIGS. 3 and 5, in the form of an initially flat strip of resilient polymeric material which has been spirally wound from end to end, heated in the spiral form to an elevated temperature below the fusion point, when cooled to return the polymeric material to its original resilient condition, resulting in a spring which, in relaxed state, assumes the form of a tight spiral with one end at the center of the spiral and the other at the outside of the spiral. The thickness of the strip from which spring 3 is made is advantageously substantially greater than that of the film of tube 1, and the spring has a substantially spring force. A force adequate to overcome the spring force of spring 3 can cause the spring to unwind into its elongated form, but reduction of that force to a value below the spring force allows the spring to return to its original spiral form. When unwound, the length of spring 3 is advantageously such that the spring extends substantially completely through the tube, though the spring can be slightly longer or slightly shorter than the tube.

Tube 1 has a first end portion 4 and a second end portion 5, portion 4 being secured to mouthpiece unit 2 in generally fluid-tight fashion. End portion 5 defines an opening 6 through which gas can escape when the tube is fully inflated. Spring 3 has a first end portion 7 and a second end portion 8, the first end portion being secured to the mouthpiece unit and the second extending to a region near opening 6.

Mouthpiece unit 2 comprises an inner member, indicated generally at 10, and an outer member, indicated generally at 11, each advantageously being an integral piece produced, e.g., by injection molding from rigid thermoplastic polymeric material. Member 10 is generally cup-shaped, including a flat wall 12 and an annular wall 13. Outer member 11 comprises a flat wall 14 and an annular wall 15. Wall 14 has a central aperture 16. A tubular mouthpiece 17 is integral with wall 14 at the periphery of aperture 16 and projects from wall 14 in the direction opposite from wall 15. Wall 14 also has a second aperture 18 which is smaller than and spaced radially from aperture 16, and a short tubular projection 19 is formed integrally with wall 14 at the periphery of aperture 18 and extends away from wall 14 in the same direction as does mouthpiece 17.

Wall 13 of member 10 includes a first outer surface portion 20 of smaller diameter and a second outer surface 21 of slightly larger diameter, portion 20 commencing wall 12 and portions 20 and 21 being joined by a transverse annular shoulder 22 facing toward wall 12. Wall 15 of member 11 includes a first inner surface portion 23 of smaller diameter, commencing at wall 14, and a second inner surface portion 24 of larger diameter, portions 23 and 24 being joined by a transverse annular shoulder 25 facing away from wall 14. Surface portions 20, 21, 23 and 24 are right circular cylindrical, the diameters of portions 20 and 21 being slightly smaller than those of portions 23 and 24, respectively. The annular free end portion of wall 15 is formed as a rounded inturned lip 26. Wall 14 is formed with a circular ridge 27, extending about the periphery of aperture 16 and projecting in the same direction as does wall 15.

Wall 12 of member 10 has a generally circular opening 28 of a diameter significantly larger than the outer diameter of ridge 27, the circular wall of opening 28 being interrupted by a straight chordal portion 29 spaced outwardly from ridge 27. Near annular wall 13 and spaced radially outwardly from wall portion 29, wall 12 has an aperture 30. The free end of wall 13 is defined by a flat transverse annular end face 31. Integrally formed with member 10 and projecting away from end face 31 is a relatively thin extension 32 of right circular cylindrical form and extending for slightly less than half the circular extent of end face 31, extension 32 embracing the area occupied by wall portion 29 and aperture 30. The outer diameter of extension 32 is slightly less than the outer diameter of end face 31. End portion 7 of spring 3 overlies the outer surface of extension 32 in flush relation and the end portion of the spring is secured to extension 32, advantageously by being stapled thereto, as shown in FIG. 3. With spring 3 thus attached to member 10, end portion 4 of tube 1 is telescoped over the spring and wall 13 of member 10 is inserted within end portion 4 of the tube until the end of the tube is beyond shoulder 22.

A check valve member 33 is now applied to outer member 11 of the mouthpiece unit. Member 33 is in the form of a normally flat flexible sheet of, e.g., polyethylene, defined by a semi-circular end edge portion 34, FIG. 4, two straight mutually parallel side edge portions 35 and an arcuate end edge portion 36, the dimensions being such that, when edge portion 36 is adjacent annular wall 13, edge portion 34 is concentric with opening 28 and that portion of member 33 which projects inwardly beyond chordal portion 29 of the wall of opening 28 is smaller than opening 28 but larger than ridge 27 of wall 12. Member 33 has an aperture 37 of the same size as aperture 18 of wall 14. Aperture 18 and projection 19 accommodate and retain a reagent tube 39, one end of tube 39 being inserted beyond wall 14 and valve member 33 being installed by passing aperture 37 over the projecting end of the reagent tube. With the valve member in place, wall 15 of member 11 is now telescoped over member 10 so that end portion 4 of tube 1 is engaged between surface portions 20 and 23 and between surface portions 21 and 24, such engagement causing the wall of tube portion 4 to be bent around shoulder 22. Telescoping of member 11 over member 10 is continued until lip 26 engages over end face 31. The relative dimensions of members 10 and 11 are such that that portion of valve member 33 having aperture 37 is clamped between walls 12 and 14, the face of wall 12 being provided with a shallow notch to accommodate the valve member so that, as seen in FIG. 3, the face of wall 12 is in direct engagement with wall 14 in all areas except that occupied by the valve member. As will be clear from comparison of FIG. 3 with FIG. 4, aperture 30 has for most of its length a diameter such as to engage reagent tube 39 in force-fit relation but, at the inner face of wall 12, is of reduced diameter, providing a shoulder 30a serving as a stop when members 10 and 11 are fully telescopically engaged. While the reagent tube is retained in force-fit fashion, the force with which the inner end of the reagent tube is embraced by projection 19 and the walls of apertures 18 and 30 is such that the tube can be removed manually from the mouthpiece unit and replaced by another tube, with such replacement being repeatable many times without damage to the device. The force-fit relation between the reagent tube and the mouthpiece unit is such that there is a seal between the exterior of the reagent tube and, e.g., the inner wall of projection 19 adequate to prevent escape of low pressure gas from within tube 1 save via the reagent tube when valve member 33 is forced against ridge 27 and, when, as seen in FIG. 2, spring 3 is acting to wind tube 1 upon itself. The structure illustrated in FIGS. 3–5 can be modified, as seen in FIG. 3A, which shoulder 25a being spaced from shoulder 22 and an elastomeric ring, such as a convention O-ring 25b applied about tube 1 to force the wall of the tube into conformation with shoulder 22, the inner diameter of ring 25b being smaller than the diameter of surface portion 20 of wall 13 so that, when applied as shown, ring 25b forces the film of the tube against surface portion 20 and shoulder 22.

Reagent tube 39 is packed with a particulate reagent or reagent composition 40 which is chosen to suit the purpose to which the device is to be put. Thus, when the device is to serve as a breath alcohol detector or analyzer, the reagent composition is one which reacts with ethyl alcohol to provide an indication of the presence in the breath of that compound, advantageously giving a colorimetric indication of both the presence of ethyl alcohol in the breath sample and the concentration of ethyl alcohol in the breath sample. Such colorimetric reagent compositions are well known in the art, and the composition 40 can be retained in the open-ended tube 39 by, e.g., inert fiber wadding 41 at each end of the tube.

Use of Device of FIGS. 1–5 to Practice the Method

To practice the method by use of the device of FIGS. 1–5 to determine presence and approximate concentration of ethyl alcohol in the breath of a human subject, the reagent tube 39, with a particulate reagent composition 40 in place, is first inserted through projection 19 and apertures 18, 30 and 37 until the end of the reagent tube engages shoulder 30a. The subject then fully inflates the lungs, places the mouth over the end of mouthpiece 17, and exhales continuously through the mouthpiece. The pressure of exhalation deflects the free portion of valve member 33 away from valve seat ridge 27 so that exhaled breath flows into tube 1. Initially, the tube is wound upon itself spirally and completely, under the force of spring 3, so that the tube and spring are in a spiral coil against mouthpiece unit 2. With exhalation continuing, exhaled breath progressively fills tube 1 until, as seen in FIG. 1, the tube is fully inflated and exhaled breath is escaping via the open end 6 of tube 1, exhalation having completely overcome the spring force of spring 3. Since the inflated volume of tube 1 is substantially less than the average human lung capacity, inflation of the tube occurs by action of breath which is not completely alveolar gas. However, as exhalation continues, all of the breath initially exhaled escapes through open end 6 and continued exhalation causes the now-inflated tube to be filled with mainly alveolar gas. Though some escape of breath from tube 1 via reagent tube 39 may occur during exhalation, the volume of gas thus escaping is small in comparison to the total inflated volume of tube 1 and has little effect upon reagent 40.

In this embodiment, the end portion 5 of tube 1, having exhaust opening 6 through which air can escape to the atmosphere when opening 6 is open, combines with second end portion 8 of spring 3 to constitute a pressure regulator which not only controls the maximum pressure within the chamber defined by the tube but also allows escape of breath via opening 6 when and so long as the pressure within the chamber, resulting from continued exhalation of breath through mouthpiece 2, exceeds the maximum. Thus, exhalation through the mouthpiece causes the combination of tube 1 and spring 3 to unwind to the condition shown in FIG. 1, with this action opening the exhaust opening 6 and breath then escaping via that opening and continuing to escape so long as the pressure resulting from exhalation is adequate to keep the tube and spring unwound and the exhaust opening open. As soon as exhalation ceases, the tube and spring commence to rewind, and rewinding occurs to such an extent that exhaust opening 6 is again closed, trapping the breath sample within the chamber defined by the tube. As a result of the tube and spring constantly tending to rewind, the rewinding action continues to apply pressure to the entrapped breath sample when exhallation ceases, since that sample can escape but slowly via opening 30 (as hereinafter described) and the rewinding of the tube and spring thus maintains the predetermined pressure in the chamber.

When the air in the subject's lungs has been completely exhausted, so that exhalation ceases, the subject removes mouthpiece 17 from the subject's mouth. Since spring 3 continuously tends to wind tube 1 upon itself, spiral winding of the tube commences and when winding has progressed through, e.g., about one half of a turn, the effect of winding is to substantially seal opening 6 at end portion 5 of the tube. Such sealing action is accentuated by the change of inflection of the tube wall at the point where the tube is changing from its inflated condition to a flattened and coiled condition. Thus, as seen in FIG. 2, the inflated portion of the tube has an inflection at 42 having curvature in one direction while the coiled portion has an inflection at 43 having a curvature in another direction. Winding of tube 1 upon itself also tends to maintain the gas pressure within the tube. The strength of spring 3 is adequate to wind the tube at such a rate that fluid pressure within the tube closes the check valve member 33 immediately and positively, so that gas cannot escape via mouthpiece 17. At this stage, winding of the tube under force applied by spring 3 continues and gas within the tube is forced outwardly through the reagent tube at a substantially constant rate until the spiral of the tube reaches the position shown in solid lines in FIG. 2 and substantially all of the sample of breath has been forced through the reagent tube.

For given sizes and characteristics of tube 1 and spring 3, the flow rate at which gas is forced from the tube via the reagent tube can be predetermined by selecting a predetermined diameter for the orifice defined by shoulder 30a and a selected resistance to gas flow presented by the packing in the reagent tube. Advantageously for colorimetric analysis, the rate of flow of gas is so predetermined that, for the particular reagent or reagents employed, a strong if not complete reaction between the breath constituent and the reagent occurs during that time required for the gas to traverse only a length, of the portion of the tube occupied by the reagent, which is small when compared to the total length of the packed body of reagent. Thus, the first portion of the breath sample driven from tube 1 into the reagent tube by the action of spring 3 reacts with the constituent in the first portion of the breath sample entering the reagent tube, and successive portions of the breath sample must travel further within the reagent tube to find a situs for reaction, so that a visible reaction front progresses along the tube and can be observed immediately through the transparent wall of the reagent tube. With tube 1 having been fully inflated to a regulated pressure, and with the latter portion of exhaled breath escaping via opening 6, the molar volume of trapped breath is known, and both the distance traversed by the visible reaction front and the color yielded by the reaction are indicative of the amount of the breath constituent present in the sample. When the method is used to determine breath alcohol content, the distance of travel of the reagent front can be correlated with the level of alcohol present in the subject's blood according to National Highway Transportation Safety Administration Standard 2003.00, January, 1977, promulgated by the United States Bureau of Standards.

Reagent systems for use in tube 39 are well known and, for ethyl alcohol, can be purchased in the trade. The method is not limited to use for analyzing breath by chemical reaction. Thus, reagent tube 39 can be replaced by a conventional collector for collecting microorganisms or by probe for determining presence of a chemical, such as ethyl alcohol aldehyde or other substance, in the breath sample, In all cases, the method has the advantages that the molar volume of the collected breath sample is known, the pressure within tube 1 remains substantially constant during that portion of exhalation after end portion 5 of tube 1 is open, and the collected breath sample is delivered at a substantially constant rate.

Device of FIG. 6

FIG. 6 illustrates diagrammatically a device according to another embodiment for practicing the method. Here, the gas collecting tube 51 is of bellows-like configuration and is provided at one end with mouthpiece unit 52 and at the other end with a pressure regulator unit indicated generally at 56, tube 51 being inherently biased toward its collapsed condition or so biased by an internal tension spring (not shown) connected at one end to unit 52 and the other end to the pressure regulator unit. Methods of manufacturing a bellows having inherent spring bias toward the collapsed condition are well known and are exemplified in U.S. Pat. No 4,079,111, Uhlig. Unit 52 has tubular mouthpiece 67, fixed to check valve member 77. A movable check valve member 88 is provided, and a compression spring 88a is arranged to bias member 88 against member 77 to close the valve. Mouthpiece unit 52 is also equipped with a lateral tubular hub 69 which opens into the mouthpiece inwardly of valve member 77 and accommodates in fluid-tight force-fit relation the inner end of reagent tube 89. Pressure regulator unit 56 comprises an outlet opening which communicates with a tube 55 accommodating a fixed check valve member 57, a movable valve member 57a, a compression spring 57b arranged to biased member 57a into closed relation against member 57, and a sound generating escape opening 57c. Though the inherent spring bias of tube 51 is sufficiently strong to collapse tube 51 to its shortest position, the spring force of the inherent bias is such that continued exhalation through mouthpiece 67, being first effective to force valve member 88 away from seat member 77, is effective to expand tube 51 to its most elongated condition, at which point further exhalation forces valve member 57a away from seat member 57 and allows gas to escape via opening 57c for so long as exhalation pressure continues. When the subject stops exhaling, valve member 57a is forced by spring 57b into seated relation against member 57; valve member 88 is forced into seating relation with member 77 by spring 88a, and (assuming stopper 89a is removed from the free end of the reagent tube) the inherent spring bias of tube 51 then collapses tube 51, forcing the collected breath sample out via tube 89.

Conversion To Sounding Device

Devices according to the invention can be converted to a sounding device simply by, e.g., removing the reagent tube 39, FIGS. 1-5, and replacing the tube with a conventional whistle, as illustrated in FIG. 7. Here, the conventional whistle 39a is equipped with a tubular adaptor 39b of the same outer diameter as the reagent tubes 39 and, after the reagent tube has been removed from the device, adaptor 39b is inserted through tubular projection 19 of outer mouthpiece member 11 until the end of the adaptor engages the shoulder at opening 30 of member 10. When the whistle has been thus installed and tube 1, FIG. 1, has been inflated by exhaled breath, spiral winding of the tube after exhalation has ceased causes the gas contained by the device to be exhausted through whistle 39a, with actuation of the whistle resulting. Thus, when use of the device with reagent tube 39 has shown a person to have an excessive breath alcohol content, replacement of the reagent tube with the whistle and repeating of the apparently normal use of the device will, in effect, "blow the whistle on" the person with excessive breath alcohol content.

What is claimed is:

1. The method for taking a sample of at least predominantly alveolar breath from a human individual and presenting that sample for testing or analysis, comprising
    providing a tubular device which is collapsible to define a chamber of smaller volume and can be expanded to increase the volume of the chamber to a predetermined value, the device having
        a mouthpiece at one end through which exhaled breath can enter the chamber,
        an escape opening communicating the chamber with the atmosphere,
        pressure regulating means normally closing the escape opening but responsive to a predetermined pressure within the chamber to allow escape of breath from the chamber via the escape opening so long as pressure within the expanded chamber is greater than or equal to said predetermined pressure, and
        resilient means biasing the chamber toward its collapsed condition of smaller volume,
        the predetermined value of increased volume being small in comparison to the lung capacity of an average human;
    requiring the individual from whom the sample is to be taken to exhale continuously through the mouthpiece until the breath in the lungs of the individual is essentially exhausted,
        initial exhalation causing the chamber to expand from its collapsed condition to the predetermined value of increased volume,
        continued exhalation then causing the pressure regulating means to allow escape of breath via the escape opening, and further exhalation then causing breath initially contained in the chamber to be discharged from the chamber so that only an alveolar breath sample remains in the chamber, and
        cessation of exhalation allowing the pressure regulating means to return to its condition of normal closure of the escape opening and thereby trap within the chamber a sample of alveolar breath of said predetermined volume, and
    allowing the trapped breath sample then to be discharged from the chamber through an outlet opening therein under the action of the resilient biasing means.

2. The method defined in claim 1, wherein the device is progressively collapsible toward the mouthpiece under the action of the biasing means; and the mouthpiece end of the device includes both an inlet through which exhaled breath enters the chamber and said outlet;
    the method further comprising
    closing the inlet when the individual has ceased to exhale; and
    directing the breath sample from the outlet through an analyzing unit as the breath sample is expelled by collapse of the chamber under the action of the resilient biasing means.

3. The method defined in claim 2, wherein
    the device comprises an elongated tube of flexible material closed at one end by the mouthpiece and open at an opposite end thereby defining the escape opening,
        the resilient means comprising a spiral spring operatively arranged to roll the tube upon itself commencing with the open end and progressing toward the mouthpiece;
    said step of requiring the individual to exhale through the mouthpiece including requiring the individual to exhale with such force as to cause the tube to unroll completely against the biasing action of the spiral spring and to then cause the exhaled breath to escape from the open end of the tube.

4. In a device for taking a sample of at least predominantly alveolar breath from a human individual and presenting that sample for testing or analysis, the combination of
    tubular means;
    a mouthpiece unit secured in fluid-tight relation to one end of the tubular means and having a discharge opening therein,
    an opposite end of the tubular means having an escape opening;
    pressure regulating means normally closing the escape opening; and
    spring means,
        the tubular means defining an expansible chamber which can be converted from an effectively shortened condition of smaller volume to an elongated condition of predetermined larger volume,
        said larger volume being substantially smaller than the lung capacity of the average human,
        the spring means being constructed and arranged to bias the tubular means toward the effectively shortened condition of smaller volume of the chamber;
    wherein continuous exhalation of breath through the mouthpiece unit into the chamber first causes the chamber to expand to its elongated condition of predetermined larger volume, further exhalation then causing the pressure regulating means to open the escape opening, and continued exhalation then resulting in continuous flow of breath through the chamber so that the breath initially filling the chamber is discharged via the escape opening, cessation of exhalation allowing the escape opening to be closed by the pressure regulating means to trap an alveolar breath sample within the chamber and the chamber then to be restored to its effectively shortened condition, while discharging the alveolar breath sample through said discharge opening by action of the spring means.

5. The combination defined in claim 4, wherein
the mouthpiece unit defines an inlet opening and the discharge opening; and
the combination further comprises
  check valve means operatively associated with the mouthpiece unit to close the inlet opening when fluid pressure in the chamber exceeds any pressure applied by exhalation through the inlet opening.

6. The combination defined in claim 4, wherein
the mouthpiece unit comprises a wall having a circumferential edge about which one end portion of the tubular means is secured, the wall having an inlet opening via which breath can be exhaled into the tubular means and an outlet opening spaced from the inlet opening;
the combination further comprising
analyzing means comprising
  a substantially rigid transparent tube having one end portion secured in the outlet opening and open to the interior of the tubular means, and
  a particulate colorimetric composition packed within the transparent tube, the particle size of the colorimetric composition and the density of packing thereof being such that the composition offers resistance to outflow of breath via the analyzing means which is large in comparison to resistance to outflow offered by the escape opening when the escape opening is not closed by the pressure regulating means.

7. The combination defined in claim 4, wherein
the tubular means comprises a tube of flexible thermoplastic polymeric material which, when extended for its full length and uninflated, has a flat configuration,
  one end portion of the tube being secured to and closed by the mouthpiece unit,
  an opposite end of the tube being open,
  the tube, when in its normal relaxed and undistorted condition, comprises a tight spiral with said one end at the outside of the spiral and said opposite end at the center of the spiral,
  the wall of the tube constituting the spring means.

8. The combination defined in claim 7, wherein
the tube is seamless.

9. The combination defined in claim 7, wherein
the tube comprises at least one longitudinally extending heat-sealed seam.

10. The combination defined in claim 4, wherein
the tubular means comprises a tube of flexible material,
  one end portion of the tube being secured to and closed by the mouthpiece unit;
  an opposite end of the tube being open; and
the mouthpiece unit comprises
  a wall having a curved circumferential edge about which one end portion of the tube is secured,
  an inlet opening via which breath can be exhaled into the tube,
  check valve means normally closing the inlet opening but displaceable to open the inlet opening in response to exhalation of breath into the tube, and
  an outlet opening spaced from the inlet opening,
the combination further comprising
analyzing means disposed in the outlet opening to receive breath forced from the tube by the action of the spring means
  the analyzing means offering resistance to outflow of breath which is substantial in comparison to resistance to outflow offered by said opposite end of the tube when said other end is open.

11. The combination defined in claim 10, wherein
the circumferential edge of the wall of the mouthpiece unit is circular, the inlet opening is generally at the center of the wall, and the outlet opening is spaced radially from the inlet opening.

12. The combination defined in claim 10, wherein
the circumferential edge of the wall of the mouthpiece unit has a long dimension and a shorter dimension and the outlet opening is spaced from the inlet opening in the direction of the longer dimension.

13. The combination defined in claim 4, wherein
the mouthpiece unit comprises
  a wall which extends traversely across said one end portion of the tubular means and has an inlet opening and a discharge opening, and
  a tubular mouthpiece communicating with the inlet opening;
the combination further comprising
check valve means comprising
  a piece of flexible polymeric film constituting a movable valve element having a first portion dimensioned to overlie and cover the inlet opening and a second portion, and
  means securing the second portion of the movable valve element against the surface of said wall which faces the interior of the tubular means.

14. The combination defined in claim 13, wherein
the mouthpiece unit further comprises
  an inner member having a wall which is engaged with said first-mentioned wall, the inner member having an opening larger than and centered generally on the inlet opening;
the second portion of the movable valve element being secured between said first-mentioned wall and said wall of the inner member.

15. The combination defined in claim 14, wherein
said first-mentioned wall has the discharge opening spaced from the inlet opening;
the second portion of the valve element has an opening registered with the discharge opening; and
the wall of the inner member has an opening registered with the discharge opening;
the combination further comprising
  a reagent tube having an end portion inserted through the discharge opening, the opening in the second portion of the valve element and the corresponding opening in the wall of the inner member.

16. The combination defined in claim 4, wherein
the tubular means comprises a tube of flexible material,
  one end portion of the tube being closed by the mouthpiece unit,
  the opposite end of the tube being open;

the spring means comprises a spiral spring operatively arranged to roll the tube upon itself commencing with the open end and progressing toward the mouthpiece unit; and the pressure regulating means comprises an end portion of the tube at said opposite end thereof and an end portion of the spiral spring which is at the center of the spiral when the spring is relaxed and undistorted.

17. The combination defined in claim 16, wherein the spring extends within the tube for at least a major portion of the length of the tube and an end portion of the spring which is at the outside of the spiral when the spring is relaxed is secured to the mouthpiece unit.

18. The combination defined in claim 17, wherein the tube is of polymeric film; and the spring is in the form of a strip of thermoplastic polymeric material disposed within the tube.

19. The combination defined in claim 18, wherein the tube comprises collapsible, non-self-supporting tubing.

20. The combination defined in claim 18, wherein the mouthpiece unit comprises an inner member about which said one end portion of the tube extends, the inner member of the mouthpiece unit including an extension projecting therefrom into the interior of the tube adjacent the wall of the tube; and the end portion of the spring which is at the outside of the spiral when the spring is relaxed is secured to said extension.

21. In a device useful as a breath analyzer and/or an amusement device, the combination of an elongated flexible tube having first and second ends;

a mouthpiece unit including an input opening and an exhaust opening, the first end of the tube being secured to the mouthpiece unit in substantially fluid tight fashion such that an individual can exhale through the input opening of the mouthpiece unit into the tube, the second end of the tube being open when the tube is extended;

spring means operative to roll the tube spirally upon itself from the second end toward the mouthpiece unit, exhalation of breath through the input opening of the mouthpiece unit into the tube being effective to inflate the tube with resultant unrolling of the tube against the action of the spring means, cessation of exhalation and closing of the input opening allowing the spring means to roll the tube upon itself with resultant closing of the second end of the tube and exhaust of the gas from within the tube via the exhaust opening; and at least one replaceable unit engageable with the mouthpiece unit at the exhaust opening to receive and conduct the gas exhausted from the tube as the tube is rolled upon itself by the spring means.

22. The combination defined in claim 21, wherein the at least one replaceable unit comprises a sound-generating device.

23. The combination defined in claim 21, wherein the flexible tube comprises collapsible, non-self-supporting tubing of polymeric material.

24. The combination defined in claim 23, wherein the wall of the tube constitutes the spring means.

* * * * *